United States Patent [19]

Hajos et al.

[11] Patent Number: 5,106,863
[45] Date of Patent: Apr. 21, 1992

[54] SUBSTITUTED IMIDAZOLE AND PYRIDINE DERIVATIVES

[75] Inventors: Zoltan G. Hajos, Princeton; Jeffery B. Press, Rocky Hill, both of N.J.; Jerry R. Roberts, Bethlehem, Pa.

[73] Assignee: Ortho Pharmaceutical Corporation, Raritan, N.J.

[21] Appl. No.: 499,146

[22] Filed: Mar. 26, 1990

[51] Int. Cl.$^5$ .................. A61K 31/415; C07D 235/04
[52] U.S. Cl. .................................... 514/395; 514/256; 514/338; 544/333; 546/271; 548/329
[58] Field of Search ................ 548/329, 327; 546/271; 544/333; 514/256, 341, 395

[56] References Cited

U.S. PATENT DOCUMENTS 3,558,775  1/1971  Fournier .......................... 514/395

FOREIGN PATENT DOCUMENTS 0190817  8/1986  European Pat. Off. ............ 514/395
62-212386  9/1987  Japan .

OTHER PUBLICATIONS

Cecil Medical Textbook Saunders Co. p. 598 (1983).
Lacova et al. "2-2,4-dinitrophenylthio . . . ", CA 92: 216176n (1982).
Bianchi et al. "Compounds with Antiulcer . . . ", CA 95: 203828k (1981).
Noyanalpan et al. "Synthesis of Some-2-(Heterocyclic . . . ", CA 101: 90831c (1984).
Paglietti et al. "2-aryl-S-benzimidazoles . . . " CA 101: 90825.
Aries et al. "Insecticidal Compositions . . . ", CA 78:39352b (1973).
Nakajima et al. "Studies on Antifungal . . . ", J. Pharm. Soc.1 Jap. 78 1378-82 (1958).

Primary Examiner—C. Warren Ivy
Assistant Examiner—Celia Chang
Attorney, Agent, or Firm—Benjamin F. Lambert

[57] ABSTRACT

Novel substituted imidazole and pyridine derivatives and their synthesis are disclosed. The derivatives inhibit the enzyme, $H^+/K^+$ ATPase, and are therefore useful for the treatment of gastrointestinal diseases.

6 Claims, No Drawings

SUBSTITUTED IMIDAZOLE AND PYRIDINE DERIVATIVES

BACKGROUND OF THE INVENTION

1. Field of the Invention

The present invention relates to novel substituted imidazole and pyridine derivatives of the general formula

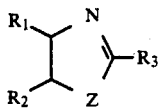

as described further below. These substituted imidazole and pyridine derivatives inhibit the enzyme, H+/K+ATPase, and as such are useful as antisecretory agents.

2. Description of the Prior Art

Specific ATPase inhibitors are substituted or unsubstituted 2-pyridylmethyl-2-benzimidazolyl sulfoxides, such as picoprazole, timoprazole and omeprazole, described in *Drugs of the Future* 6, 77 (1981); 7, 899 (1982); and 8, 1040 (1983).

A variety of benzimidazoles with a terpene chain and related compounds such as 1-geranyl- and 1-neryl-benzimidazoles have been described in *Agric. Biol. Chem.* 48, 1617 (1984) and Japanese Patent Application 59,187,263, published Oct. 15, 1984. These compounds are reported as having juvenile hormonal activity and insecticidal activity.

SUMMARY OF THE INVENTION

The present invention is directed to substituted imidazole and pyridine derivatives of the general formula

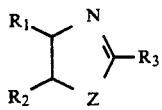 I where

Z may be —CH=CH— or —N—R$_4$;

R$_1$ and R$_2$ may together form a double bond or may together form a six-membered ring of the formula

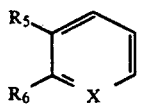 when Z is —N—R$_4$;

R$_3$ may be hydrogen, C$_1$-C$_6$ alkyl, C$_1$-C$_4$ alkoxy, phenyl, substituted phenyl, C$_2$-C$_6$ alkenyl, C$_2$-C$_6$ alkynyl, C$_4$-C$_{16}$ alkadienyl, phenyl C$_2$-C$_6$ alkenyl, heteroaryl such as thienyl, pyridyl furyl and pyrimidinyl, substituted heteroaryl, —S—R$_7$ or —CH$_2$—S—R$_8$;

wherein the substituted phenyl and substituted heteroaryl may be substituted with C$_1$-C$_4$ alkyl, C$_1$-C$_4$ alkoxy, hydroxy, halogen, CF$_3$, nitro or mercapto C$_1$-C$_4$ alkyl;

R$_4$, R$_7$ and R$_8$ may be the same or different and may be hydrogen, C$_1$-C$_{15}$ straight or branched chain alkyl, allyl, C$_1$-C$_4$ alkoxy, phenyl, substituted phenyl, C$_1$-C$_{20}$ alkenyl, C$_2$-C$_6$ alkynyl, C$_4$-C$_{16}$ alkadienyl, phenyl C$_2$-C$_6$ alkenyl, CH$_2$-heteroaryl such as CH$_2$-thienyl, CH$_2$-pyridyl, CH$_2$-furyl and CH$_2$-pyrimidinyl or CH$_2$-substituted heteroaryl;

wherein the substituted phenyl and substituted heteroaryl may be substituted with C$_1$-C$_4$ alkyl, C$_1$-C$_4$ alkoxy, hydroxy, halogen, CF$_3$, nitro or mercapto C$_1$-C$_4$ alkyl;

R$_5$ and R$_6$ may be the same or different and may be hydrogen, C$_1$-C$_4$ alkyl, C$_1$-C$_4$ alkoxy, C$_2$-C$_4$ acyloxy, hydroxy, amino, C$_2$-C$_4$ acylamino, C$_1$-C$_4$ alkylamino, trifluoromethyl, nitro or halogen; and X may be C or N;

with the provisos that when Z is —CH=CH—, R$_3$ is —CH$_2$—S—R$_8$, when Z is —N—R$_4$ and R$_1$ and R$_2$ together form a double bond, R$_3$ is —S—R$_7$ and when X is N, R$_3$ is —S—R$_7$ and R$_5$ and R$_6$ are both hydrogen.

More specifically, and for ease of reference, the present invention relates to thiobenzimidazoles, benzimidazoles, mercaptoimidazopyridines, mercaptoimidazoles, and thiomethyl pyridines shown below in formulas IA, IB, IC, ID and IE, respectively.

The thiobezimidazoles of the present invention are represented by the formula

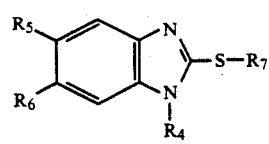 IA where R$_4$, R$_5$, R$_6$ and R$_7$ are as defined above.

The compounds of the present invention wherein X is C or N are represented by the formula

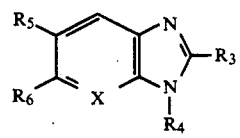 IB where R$_3$, R$_4$, R$_5$ and R$_6$ are as defined above.

The mercaptoimidazopyridines of the present invention are represented by the formula

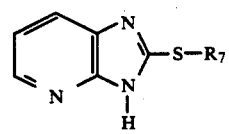 IC where R$_7$ is as defined above.

The mercaptomidazoles of the present invention are represented by the formula

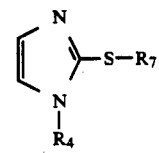 ID where R$_4$ and R$_7$ are as defined above.

The thiomethylpyridines of the present invention are represented by the formula

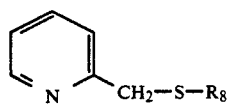

where R$_8$ is as defined above.

The compounds of the above formulas (formulas I, IA, IB, IC, ID and IE) are useful as antisecretory agents due to their ability to inhibit the enzyme, H$^+$/K$^+$AT-Pase.

DETAILED DESCRIPTION OF THE INVENTION

The invention in its broadest aspects relates to substituted imidazole and pyridine derivatives which have antisecretory activity, and are therefore useful for the treatment of gastrointestinal diseases in mammals The compounds which posses this antisecretory activity are shown in formulas I, IA, IB, IC, ID and IE above.

The preferred compounds of the present invention are those of formula I in which R$_3$ is hydrogen, methyl, hydroxymethyl, CO$_2$CH$_3$, CH$_2$CO$_2$CH$_3$, mercaptomethylphenyl, —S—R$_7$ or —CH$_2$—S—R$_8$;

R$_4$ is hydrogen, neryl, citronellyl, octyl, cyclohexyl, geranyl or a substituted heteroaryl of the formula

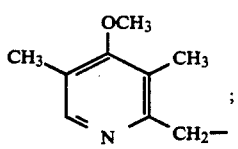

R$_5$ is hydrogen, halogen or methoxy;

R$_6$ is hydrogen, halogen, methoxy or trifluoromethyl;

R$_7$ is geranyl, octyl, neryl, citronellyl 1-, 2- or 3-picolyl or CH$_2$CO$_2$CH$_3$; and R$_8$ is hydrogen, acetyl, C$_{1-15}$ straight or branched chain alkyl, allyl, or heteroaryl such as thienyl, pyridyl, furyl and pyrimidinyl.

The compounds of formula I in which Z is —N—R$_4$, R$_3$ is —S—R$_7$ and R$_1$ and R$_2$ are combined to form the six-membered ring

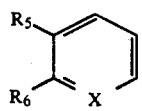

in which X is C are prepared by Scheme I shown below.

SCHEME I

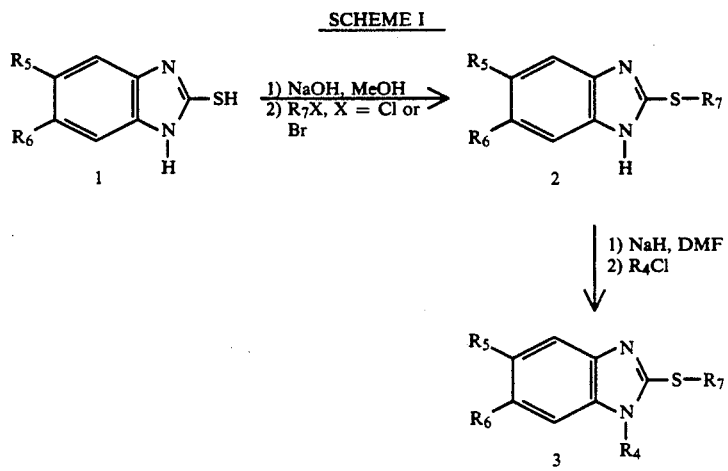

The synthesis of these compounds was accomplished by treatment of the appropriately substituted 2-mercaptobezimidazole (1) with a chloride or bromide of the R$_7$ group in sodium hydroxide/methanol to give the appropriately 2-substituted thiobenzimidazole (2). The reaction of the 2-substituted thiobenzimidazole (2) with sodium hydride in dimethylformamide and the appropriate halide gave the N-1 substituted 2-substituted thiobenzimidazole (3). 2-Mercaptobenzimidazole was obtained from Aldrich Chemical Co., Milwaukee, Wis., and 5-fluoro-6-chloro-2-mercaptobenzimidazole was obtained from Maybridge Chemical Co., U.K. For synthesis of 5-chloro- and 5-methoxy-2-mercaptobenzimidazole, see Varima, R. S., J. Indian Chemical Soc. 62, 73 (1985), and for synthesis of 5-trifluoromethyl-2-mercaptobenzimidazole, see Senn-Bilfingen, J., DE 3240298 (1983).

The compounds of formula I in which Z is —N—R$_4$, R$_3$ is other than —S—R$_7$ and R$_1$ and R$_2$ are combined to form the six-membered ring

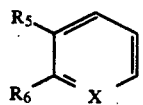

in which X is C are prepared as shown below in Scheme II. These compounds are also recognized as the benzimidazoles of formula IB.

SCHEME II

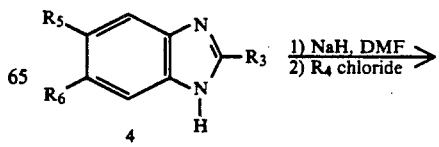

-continued
SCHEME II

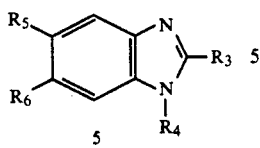

An appropriate 2-substituted benzimidazole (4) is reacted with sodium hydride and a chloride of the R4 group in dimethylformamide The N-1(R4-substituted)-2-substituted benzimidazole (5) is the resultant product.

The compounds of formula I in which Z is CH=CH—, $R_3$ is —S—$R_7$ and $R_1$ and $R_2$ are combined to form the six-membered ring in which X is N are prepared as shown below in Scheme III. These compounds are also recognized as the mercaptoimidazopyridines of formula IC.

SCHEME III

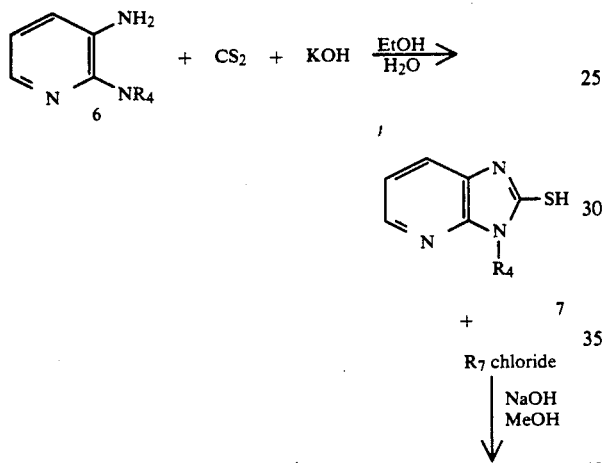

-continued
SCHEME III

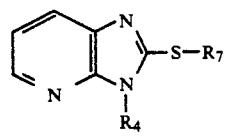

An R4-substituted 2,3-diaminopyridine (6) is reacted with carbon disulfide in a potassium hydroxide/ethanol solvent to yield a substituted 2-mercaptoimidazopyridine (7). The substituted 2-mercaptoimidazopyridine (7) is then reacted with a chloride of the R7 group as defined above, in a sodium hydroxide/methanol solvent to produce the 2-mercapto-substituted-imidazopyridine (8).

The compounds of formula I in which Z is —N—$R_4$, $R_3$ is —S—$R_7$ and $R_1$ and $R_2$ combine to form a double bond are prepared as shown below in Scheme IV. These compounds are also recognized as the mercaptoimidazoles of formula ID.

SCHEME IV

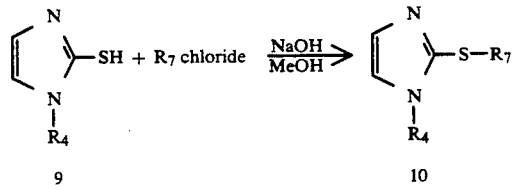

A 1-substituted-2-mercaptomidazole (9) is reacted with the chloride of the R7 group in a basic solvent of sodium hydroxide and methanol to yield the 1-(R4-substituted)-2-mercapto(R7-substituted)imidazole (10).

The compounds of formula I in which Z is —CH=CH—, $R_3$ is —$CH_2$—S—$R_8$ and $R_1$ and $R_2$ combine to form a double bond are prepared as described below in Scheme V. The compounds are also recognized as the thiomethylpyridines of formula IE.

SCHEME V

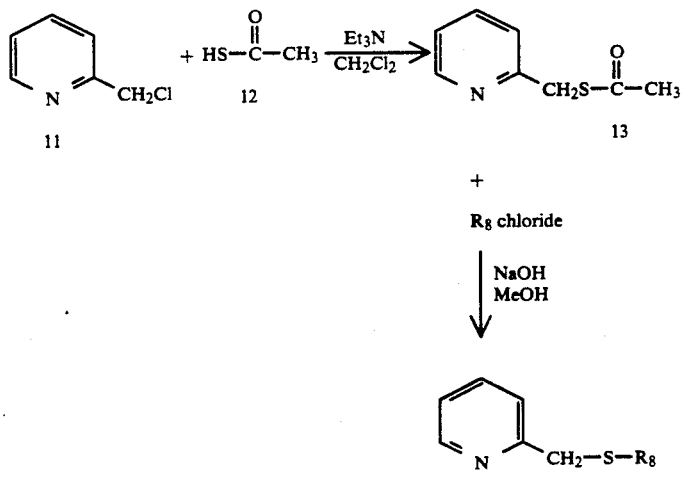

The reaction of 2-picolylchloride (11) with thioacetic acid (12) in Et3N/CH2Cl2 gives 2-picolylthioacetate (13). The 2-picolylthioacetate (13) is then reacted with a chloride of the $R_8$ group in NaOH/MeOH to give the $R_8$-substituted thiomethylpyridine (14).

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to illustrate but not limit the invention.

EXAMPLE 1

2-[(3,7-Dimethyl-2,6(E)-octadienyl)-thio]-1H-1,3-benzimidazole

To a suspension of sodium hydride (NaH) (0.69 g, 30 mmol) in dimethylformamide (DMF) (100 mL) was added 2-mercaptobenzimidazole (4.5 g, 10 mmol) in DMF (20 mL) at 0° C. under $N_2$. To the resultant solution was added geranyl chloride (5.16 g, 10 mmol) over 30 minutes. The reaction was stirred for five hours at ambient temperature under $N_2$ then treated with 2N NaOH and extracted with diethyl ether ($Et_2O$). The $Et_2O$ extract was washed with saturated NaCl, concentrated in vacuo, dissolved in methylene chloride, and dried over $Na_2SO_4$. Recrystallization from $Et_2O$ gave white crystalline 2-[(3,7-dimethyl-2,6(E)-octadienyl)-thio]-1H-1,3-benzimidazole (3.15 g, 36.6%). m.p. 98°–100° C. NMR $(CDCl_3)$:$\delta$7.4(m, 2H), 7.1(m, 2H) 5.3(t,J=8 Hz, 1H) 5.0(m 1H) , 3.90(d, J=10 Hz, 2H , 2.00(m, 4H), 1.65(m, 9H).

Anal. Calcd. for
$C_{17}H_{22}N_2S$: C,71.28; H,7.74; N,9.78.
Found: C,70.75; H,7.75; N,9.53.

EXAMPLE 2

5-Chloro-2-[(3,7-dimethyl-2,6(E)-octadienyl)-thio]-1H-1,3-benzimidazole

A solution of 4-chloro-o-phenylenediame (4.25 g, 30 mmol) in $H_2O$ (4.5 mL), KOH (1.9 g, 34 mmol), ethanol (30 mL), and $CS_2$ (2.6 g, 34 mmol) was refluxed for 3 hours and stirred at ambient temperature overnight. Evaporation gave a residue which was dissolved in $CH_2Cl_2$ and acidified to pH 5 with 2N HCl. Filtration of the resultant precipitate gave 2.59 g of 5-chloro-2-mercaptobenzimidazole.

To a solution of the 5-chloro-2-mercaptobenzimidazole (0.665 g, 3.6 mmol) in methanol (10 mL) and 2N NaOH (7 mmol) was added geranyl chloride (0.775 g, 4.5 mmol). The reaction mixture was stirred at ambient temperature for 24 hours, evaporated in vacuo, dissolved in $CH_2Cl_2$, washed with water, and dried over $Na_2SO_4$. Evaporation and flash chromatography (Merck Kieselgel, $CH_2Cl_2$) gave an oil which was crystallized with pentane to yield a white solid of the title compound (270 mg). m.p. 102°–104° C. NMR $(CDCl_3)\delta$7.45–7.0(m,3H), 5.37(t, J=7 Hz,1H), 5.03(t,J=7Hz, 1H), 3.93(d,J=8 Hz,2H), 2.02(m,4H), 1.67(s,3H), 1.66(s,3H), 1.58(s,3H).

Anal. Calcd. for
$C_{17}H_{21}ClN_2S$: C,63.63; H,6.60; N,8.73.
Found: C,64.00; H,6.76; N,8.57.

EXAMPLE 3

6-Chloro-5-fluoro-2-[(3,7-dimethyl-2,6(E)-octadienyl) thio]-1H-1,3-benzimidazole.¼Hydrate To a solution of 6-chloro-2-mercaptobenzimidazole (2.02 g, 10 mmol) in methanol (20 mL) was added 2N sodium hydroxide (10 mmol). To the resultant solution was added geranyl chloride (1.72 g, 10 mmol) and methanol (10 mL). After stirring 16 hours at ambient temperature, the solution was evaporated in vacuo and the resultant solid dissolved in methylene chloride, washed with water, saturated sodium chloride and dried over $Na_2SO_4$. Evaporation of the solvent gave a light beige solid of the title compound (2.72 g, 80%). m.p. 122°–124° C.

Anal. Calcd. for
$C_{17}H_{21}ClFN_2S \cdot \tfrac{1}{4}H_2O$: C,59.46; H,6.02; N,8.16.
Found: C,59.39; H,5.86; N,8.26.

EXAMPLE 4

2-[(3,7-Dimethyl-2,6(E)-octadienyl)thio]-5-methoxy-1H-1,3-benzimidazole Monooxalate To potassium hydroxide (3.8 g, 0.067M) in ethanol (20 mL) and water (7 mL) was added 2.5 mL $CS_2$ (3.09 g, 0.04M) ($H_2S$ trapped over clorox). The reaction mixture was stirred for 30 minutes at ambient temperature, cooled to 0° C., and 4-methoxy-o-phenylene diamine (5.23 g, 0.03M) was slowly added. This reaction mixture was then stirred at reflux for 4 hours, stirred at ambient temperature overnight (basic soln. with pH paper), evaporated in vacuo and diluted with $CH_2Cl_2$. Addition of water gave a precipitate which was suspended in $CH_2Cl_2$ and acidified to pH 4. Filtration of the suspension gave purple crystalline 5-methoxy-2-mercaptobenzimidazole (3.4 g, 63%).

To the 5-methoxy-2-mercaptobenzimidazole (2.5 g, 0.014M) in methanol (100 mL) was added geranyl chloride (2.4 g, 0.014M). The solution was taken to pH 11 (2N NaOH), stirred overnight at ambient temperature, evaporated, dissolved in $CH_2Cl_2$, washed with saturated $NaHCO_3$+brine, and dried over $Na_2SO_4$. The solvent was evaporated to oil which was flash chromatographed (Rf=0.76) (5% MeOH ($CH_2Cl_2$)) to give 2-[(3,7-dimethyl-2,6-(E)-octadienyl)thio]-5-methoxy-1H-1,3-benzimidazole (free base) which was converted to its oxalate salt (0.74 g). m.p. 113°–116° C. NMR (DMSO-d$_6$)δ7.8(m,3H), 5.2 (m, 2H), 3.9(d, J=7 Hz, 2H), 3.8(s, 3H), 2.02(m, 4H),1.7(s,3H), 1.6(s, 6H).

Anal. Calcd. for
C$_{18}$H$_{24}$N$_2$OS.(COOH)$_2$: C,59.08; H,6.45; N,6.89. Found: C,59.44; H,6.63; N,6.83.

EXAMPLE 5

1-(3,5-Dimethyl-4-methoxy-2-pyridylmethyl)-2-[(3,7-dimethyl-2,6(E)-octadienyl)thio]-1H-1,3-benzimidazole Monooxalate Hemihydrate To a solution of 2-[(3,7-dimethyl-2,6(E)-octadienyl)-thio]-1H-1,3-benzimidazole from Example 1 (1.5 g, 5.2 mmol) and 3,5-dimethyl-4-methoxy-2-pyridylmethyl chloride (0.465 g, 5 2 mmol) in dimethylformamide (7 mL) at 0° C. under nitrogen was added dropwise triton-B (5 mL of a 40% solution). The solution was stirred at ambient temperature for 72 hours, then at 50° C. for 48 hours. Evaporation of the solvent gave a residue which was dissolved in CH$_2$Cl$_2$, washed with water and dried over Na$_2$SO$_4$. Evaporation of the solvent and flash chromatography of the resultant oil (10% Et$_2$O/CH$_2$Cl$_2$, Merck Kieselgel) gave 1.1 g of 1-(3,5-dimethyl-4-methoxy-2-pyridylmethyl)-2-[(3,7-dimethyl-2,6(E)-octadienyl)thio]-1H-1,3-benzimidazole (free base) which was converted to its oxalate salt (1.36 g). m.p. 76°–80° C. NMR (DMSO-d$_6$) δ7.93(s,1H), 7.5(m,1H), 7.1(m,3H), 5.4(s,2H), 5.37(m,1H), 5.07(m,1H), 3.93(m,2H), 3.70(s,3H), 2,27(s,3H), 2.15(s,3H), 2.0(m,4H), 1.6(s,3H), 1.53(s,3H), 1.07(s,3H).

Anal. Calcd. for
C$_{26}$H$_{33}$N$_3$OS.(COOH)$_2$.½H$_2$O: C,62.89; H,6.79; N,7.86.

Found: C,67.92; H,6.45; N,7.83.

EXAMPLE 6

5-Trifluoromethyl-2-[(3,7-dimethyl-2,6(E)-octadienyl)-thio]-1H-1,3-benzimidazole To a solution of 5-trifluoromethyl-2-mercaptobenzimidazole (1.09 g, 5 mmol) (Senn-Bilfingen, J., DE 3240298(1983)) in methanol (10 mL) was added 2N aqueous sodium hydroxide (6 mmol) and geranyl chloride (0.86 g, 5 mmol). The resultant solution was stirred for 48 hours at ambient temperature, evaporated in vacuo, dissolved in methylene chloride, washed with saturated sodium chloride, and dried over sodium sulfate. Evaporation of the solvent gave an oil which was flash chromatographed (5% MeOH (CH$_2$Cl$_2$) in Merck Kieselgel) and treated with charcoal. Evaporation of the solvent gave an off-white solid of the title compound (550 mg). m.p. 106°–108° C. NMR (CDCl$_3$)δ7.83(m,1H), 7.57(m,2H), 5.43(d, J=7 Hz,1H), 5.2(m,1H), 4.03(d,J=7Hz,2H), 2.0(m,4H), 1.70(s,3H), 1.67(s,3H), 1.65(s,3H).

Anal. Calcd. for
C$_{18}$H$_{21}$F$_3$N$_2$S: C,61.00; H,5.47; N,7.90. Found: C,61.53; H,6.25; N,7.81.

EXAMPLE 7

3S(+)-2-[(3,7-Dimethyl-6-octen-1-yl)thio]-1H-1,3-benzimidazole

To a solution of citronellyl chloride (1.72 g, 10 mmol) in methanol (10 mL) and 2N NaOH (10 mmol) was added 2-mercaptobenzimidazole (1.5 g, 10 mmol). The solution was heated at 65° C. for 24 hours, evaporated, dissolved in CH$_2$Cl$_2$, washed with saturated sodium chloride, and dried over Na$_2$SO$_4$. Evaporation of the solvent and flash chromatography (10% Et$_2$O/CH$_2$Cl$_2$, Merck Kieselgel) gave 1.46 g of the title compound after evaporation. m.p. 58°–60° C. NMR (CDCl$_3$)δ9.56(br,1H), 7.26(m,4H), 5.07(m,1H), 3.37(m,2H), 1.85(m,2H), 1.7(s,3H), 1.57(s,3H), 1.30(m,5H), 0.91(d, J=6Hz,2H).

Anal. Calcd. for
C$_{17}$H$_{24}$N$_2$S: C,70.78; H,8.39; N,9.71. Found: C,70.72; H,8.44; N,9.69.

EXAMPLE 8

(+)-2-[(3,7-Dimethyl-6-octen-1-yl)sulfinyl]-1H-1,3-benzimidazole Monooxalate

To a solution of (±) citronellyl chloride (3.44 g, 20 mmol) in methanol (10 mL) and 2N NaOH/H$_2$O (25 mmol) was added 2-mercaptobenzimidazole (3.0 g, 20 mmol). The solution was stirred at gentle reflux for 72 hours, evaporated, dissolved in CH$_2$Cl$_2$, washed with brine, and dried over Na$_2$SO$_4$. Evaporation and flash chromatography (10% Et$_2$O/CH$_2$Cl$_2$, Kieselgel (Merck)) gave 4.87 g (85%) of a sulfide of 3S(+)-2-[(3,7-dimethyl-6-octen-1-yl)thio]-1H-1,3-benzimidazole. To a solution of the 3S(+)-2-[ 3,7-dimethyl-6-octen-1-yl]thio]-1H-1,3-benzimidazole 2.3 g, 8 mmol) in CH$_2$Cl$_2$ (30 mL) a 0° C. was added MCPBA (1.4 g, 8 mmol) over 1 hour. The solution was stirred at 0° C. for 3 hours, washed with Na$_2$SO$_3$, saturated NaHCO$_3$, and brine, and then dried over Na$_2$SO$_4$. Evaporation and flash chromatography (Merck Kieselgel, 50% Et$_2$O/CH$_2$Cl$_2$) gave 1.74 g of (+)-2-[(3,7-dimethyl-6-octen-1-yl)sulfinyl]-1H-1,3-benzimidazole which was converted to its oxalate salt to give 1.40 g. m.p. 122°–124° C. NMR (DMSO-d$_6$)δ12.05(br,1H), 7.44(m,1H), 7.33(m,3H), 5.00(t,J=8 Hz,1H), 3.32(m,2H), 1.85(m,2H), 1.65(s,3H), 1.53(s,3H), 1.30(m,5H), 0.89(d,J=6 Hz,2H).

Anal. Calcd. for
C$_{19}$H$_{26}$N$_2$O$_5$S: C,57.85; H,6.64; N,7.10. Found: C,57.83; H,6.75; N,7.03.

EXAMPLE 9

1-(3,5-Dimethyl-4-methoxy-2-pyridylmethyl)-2-[(3,7-dimethyl-6-octen-1-yl)thio]-1H-1,3-benzimidazole Monooxalate To a suspension of sodium hydride (0.23 g, 10 mmol) in dimethylformamide (15 mL) at 0° C. under nitrogen was added 3S(+)-2-[(3,7-dimethyl-6-octen-1-yl)thio]-1H-1,3-benzimidazole (free base) (2.3 g, 7.8 mmol) from Example 7 in dimethylformamide (15 mL). After 10 minutes of stirring, 3,5-dimethyl-4-methoxy-2 -pyridylmethyl chloride (1.5 g, 9.5 mmol) in dimethylformamide (15 mL) was added and the reaction mixture was stirred at ambient temperature for 3 days, poured over ice, extracted into CH$_2$Cl$_2$, and evaporated in vacuo to give 3.19 g crude 1-(3,5-dimethyl-4-methoxy-2-pyridylmethyl)-2-[(3 ,7 -dimethyl-6-octen-1-yl)thio]-1H-1,3-benzimidazole. The residue as flash chromatographed (Merck Kieselgel, 10% Et$_2$O/CH$_2$Cl$_2$) to give 1.96 g of the free base of the title compound as an oily residue of which 600 mg was converted to the oxalate salt to give 500 mg as a white solid. m.p. 76°–78° C. NMR (DMSO-d$_6$) δ7.9(s,1H), 7.35(m,4H), 5.40(s,2H), 3.70(s,3H), 3.28(m,2H), 2.27(s,3H), 1.97(s,3H), 1.70(m,2H), 1 63(s,3H), 1.53(s,3H), 1.40(m,5H), 0.87(s,3H).

Anal. Calc. for
C$_{26}$H$_{35}$N$_3$OS.(COOH)$_2$: C,63.73; H,7.07; N,7.96. Found C,63.44; H,7.27; N,8.07.

EXAMPLE 10

1-(3,7-Dimethyl-2,6(Z)-octadienyl)-2-[(3,7-dimethyl-2,6(Z)-octadienyl)-thio]-1H-1,3-benzimidazole Monooxalate To a suspension of sodium hydride (0.115 g, 5 mmol) in dimethylformamide (5 mL) at 0° C. under nitrogen was added 2-[(3,7-dimethyl-2,6(%)-octadienyl)thio]-1H-1,3-benzimidazole (1.43 g, 5 mmol) from Example 11, below in dimethylformamide (25 mL). The solution was stirred at ambient temperature for 15 minutes, then neryl chloride (0.86 g, 5 mmol) in dimethylformamide (15 mL) was added. After stirring at ambient temperature overnight, the solution was evaporated in vacuo, dissolved in $CH_2Cl_2$, washed with saturated $NaHCO_3$, and dried over $Na_2SO_4$. Evaporation of the solvent gave an oil which was flash chromatographed (Merck Kieselgel, $CH_2Cl_2$) to give 1.5 g of 1-(3,7-dimethyl-2,6(Z)-octadienyl)-2-[(3,7-dimethyl-2,6(Z)-octadienyl)-thio]-1H-1,3-benzimidazole as an oil which was converted to its oxalate salt to give 800 mg of a white solid. m.p. 55°–58° C. NMR (DMSO-$d_6$)$\delta$7.5(m, 4H), 5.25(m, 4H), 4.70(d, J=8 Hz, 2H), 4.05(d, J=8 Hz, 2H), 2.20(m, 8H), 1.75(s, 6H), 1.70(s, 12H).

Anal. Calcd. for
$C_{27}H_{38}N_2S.(COOH)_2$: C,67.93; H,7.86; N,5.41.
Found: C,68.03; H,7.75; N,5.27.

EXAMPLE 11

2-[(3,7-Dimethyl-2,6(Z)-octadienyl)-thio]-1H-1,3-benzimidazole.¼Hydrate

To a solution of 2-mercaptobenzimidazole (5.1 g, 34 mmol) and 2N $NaOH/H_2O$ (pH 11) in methanol (100 mL) was added neryl chloride (5.85 g, 34 mmol). The reaction mixture was stirred at ambient temperature for 16 hours, evaporated in vacuo, dissolved in $CH_2Cl_2$, washed with saturated $NaHCO_3$ and brine, and dried over $Na_2SO_4$. Evaporation of the solvent gave an oil which was flash chromatographed (Merck Kieselgel, 5% $MeOH/CH_2Cl_2$) to give the title compound which was crystallized from $Et_2O$/pentane to give a white solid (3.4 g, 35%). m.p. 98°–101° C. NMR (CDCl$_3$)$\delta$7.35(m 4H) 5.25(m 2H) 4.0(d,J=6 Hz,2H), 2.05(m,4H), 1.68(s,3H), 1.62(s,3H), 1.60(s,3H).

Anal. Calcd. for
$C_{17}H_{22}N_2S.\frac{1}{4}H_2O$: C,70.17; H,7.67; N,9.63.
Found: C,70.28; H,7.77; N,9.63.

EXAMPLE 12

2-Octylthio-1H-1,3-benzimidazole

To a solution of 2-mercaptobenzimidazole (4.95 g, 33 mmol) in methanol (150 mL) and 2N $NaOH/H_2O$ (50 mmol) was added octyl bromide (7.16 g, 33 mmol). The solution was stirred at ambient temperature for 72 hours, during which a suspension formed which was filtered and the solid residue dissolved in $CH_2Cl_2$, washed with saturated $NaHCO_3$, and dried over $Na_2SO_4$. Evaporation of the solvent gave the title compound as a white solid (6.2 g, 72%). m.p. 110°–113° C. NMR CDCl$_3$)$\delta$7.4(m, 4H), 3.22(t, J=8 Hz, 2H), 1.20(br, 15H).

Anal. Calcd. for
$C_{15}H_{22}N_2S$: C,68.45; H,8.45; N,10.68.
Found: C,68.35; H,8.40; N,10.61.

EXAMPLE 13

5-Methoxy-2-octylthio-1H-1,3-benzimidazole Hemioxalate Monohydrate

To a solution of 5-methoxy-2-mercaptobenzimidazole (2 16 g, 12 mmol) (Varima, R. S., *J. Indian Chem. Soc.* 62, 73 (1985)) in methanol (100 mL) and 2N $NaOH/H_2O$ (20 mmol) was added octyl bromide (2.65 g, 12 mmol). The solution was stirred at ambient temperature for 16 hours, evaporated, dissolved in $CH_2Cl_2$, washed with saturated $NaHCO_3$, and dried over $Na_2SO_4$. Evaporation of the solvent and flash chromatography (Merck Kieselgel, 5% $MeOH/CH_2Cl_2$) gave 1.4 of the title compound as a free base. Conversion of 600 mg of the free base to its oxalate salt gave 540 mg of a white solid. m.p. 102°– 106° C. NMR (DMSO-$d_6$)$\delta$7.10(m,3H), 3.25(t,J=4 Hz,2H), 1.20(br, 15H).

Anal. Calcd. for
$C_{16}N_{24}N_2OS.\sim(COOH)_2.H_2O$: C,57.43; H,7.65; N,7.88.
Found: C,57.72; H,7.26; N,7.56.

EXAMPLE 14

5-Chloro-2-octylthio-1H-1,3-benzimidazole

To a solution of 5-chloro-2-mercaptobenzimidazole (1.84 c, 10 mmol) (Varima, R. S., *J. Indian Chem. Soc.* 62, 73 (1985)) in methanol (10 mL) and 2N sodium hydroxide (13 mmol) was added octyl bromide (2.17 g, 10 mmol). The solution was stirred at ambient temperature for 72 hours, evaporated, dissolved in $CH_2Cl_2$, washed with brine and dried over $Na_2SO_4$. Evaporation of the solvent and flash chromatography (Merck Kieselgel, 5% $Et_2O/CH_2Cl_2$) gave a residue which solidified on standing. A pentane wash gave the title compound as a beige solid (2.23 g), m.p. 66°–67° C. NMR (CDCl$_3$)$\delta$7.3(m, 3H), 5.33(t, J=6 Hz, 2H), 1.20(br, 15H).

Anal. Calcd. for
$C_{15}H_{21}ClN_2S$: C,60.69; H,7.13; N,9.44.
Found: C,60.32; H,7.50; N,9.35.

EXAMPLE 15

2-[3,7-Dimethyl-2,6(E)octadienylthiomethyl]-pyridine.1/10 Hydrate

A solution of 2-picolylchloride (6.73 g, 53 mmol) and thioacetic acid (53 mmol) in $CH_2Cl_2$ (100 mL) and $Et_3N$ (21.2 g, 210 mmol) was stirred 16 hours at ambient temperature, washed with saturated $NaHCO_3$, and dried over $Na_2SO_4$. Evaporation of the solvent and flash chromatography (Merck Kieselgel, 5% $MeOH/CH_2Cl_2$) gave 6.2 g (70%) of 2-picolylthioacetate as a brown oil. A solution of the 2-picolylthioacetate (4.6 g, 30 mmol) and geranyl chloride (5.16 g, 30 mmol) in methanol (60 mL) and 2N $NaOH/H_2O$ (50 mmol) was stirred at ambient temperature for 16 hours, evaporated, dissolved in $CH_2Cl_2O$, washed with water, and dried over $Na_2SO_4$. Evaporation of the solvent and flash chromatography (Merck Kieselgel, 5% $MeOH/CH_2Cl_2$) gave 6.1 g (78%) of the title compound as a brown oil. NMR (CDCl$_3$)$\delta$8.20(d, J=6 Hz, 1H), 7.50(m, 3H), 5.20(m, 2H), 4.80(s, 2H), 3.20(d, J=6 Hz, 2H), 2.10(m, 4H), 1.80(s, 3H), 1.61(s, 3H), 1.59(s, 3H).

EXAMPLE 16

2-[(3.7-Dimethyl-2,6(E)-octadienyl)thio]-1H-imidazo[4,5-6]pyridine Monooxalate Hemihydrate A solution of 2,3-diaminopyridine (10.0 g, 92 mmol), potassium hydroxide (6.8 g, 123 mmol)k, $CS_2$ (9.4 g, 123 mmol), ethanol (100 mL), and water (20 mL) was stirred at reflux for 5 hours, then at ambient temperature overnight. Evaporation in vacuo gave a residue which was dissolved in $CH_2Cl_2$, acidified to pH 5 with 2N hydrochloric acid, and stirred for 1 hour. The resultant suspension was filtered to give 15.7 g of 2-mercaptoimidazopyridine as a brown solid. A solution of the 2-mercaptoimidazopyridine (4.23 g, 28 mmol) and geranyl chloride (4.8 g, 28 mmol) in methanol (40 mL) and 2N $NaOH/H_2O$ (40 mmol) was stirred in 16 hours at ambient temperature, evaporated, dissolved in $CH_2Cl_2$, washed with water, and dried over $Na_2SO_4$. Flash chromatography (Merck Kieselgel, 5% $MeOH/CH_2Cl_2$) gave 2.0 g (25%) of 2-[(3,7-dimethyl-2,6(E)-octadienyl)-thio]-1H-imidazo[4,5-6]pyridine, 1.0 g of which was converted to its oxalate salt. m.p. 118°–121° C. NMR (DMSO-$d_6$)δ8.20(d, J=5 Hz, 1H), 7.60(m, 2H), 5.40(d, J=7 Hz, 1H), 5.10(d, J=6 Hz, 1H), 4.00(d, J=6 Hz, 2H), 2.00(m, 4H), 1.70(s, 3H), 1.61(s, 3H), 1.60(s, 3H).

EXAMPLE 17

3S-2-[(3,7-Dimethyl-6-octen-1-yl)thio]-1-methylimidazole

A solution of 1-methyl-2-mercaptoimidazole (1.7 g, 15 mmol) in methanol (8 mL), S-(-)-citronellyl chloride (0.89 g, 5.2 mmol) and 2N $NaOH/H_2O$ (5 mmol) was stirred at ambient temperature for 48 hours then at 50° C. for 72 hours. Evaporation in vacuo gave a residue which was dissolved in $CH_2Cl_2$, washed with saturated sodium chloride, and dried over $Na_2SO_4$. Evaporation of the solvent and flash chromatography (Merck Kieselgel, 10% $Et_2O/CH_2Cl_2$) gave an oil which on conversion to a hydrochloride salt gave 700 mg of the title compound as a beige solids. m.p. 83°–86° C. NMR (DMSO-$d_6$)δ7.75(d, J=8 Hz, 2H), 5.07(m, 1H), 3.78(s, 3H), 3.33(d, J=8 Hz, 2H), 1.95(m, 2H), 1.67(s, 3H), 1 55(s, 3H), 1.37(m, 3H), 0.90(s, 3H).
Anal. Calcd. for
$C_{14}H_{24}N_2S.HCl.\frac{3}{8}H_2O$: C,55.88; H,8.82; N,9.31.
Found: C,55.92; H,8.77; N,9.15.

EXAMPLE 18

1-(3,7-Dimethyl-2,6(E)-octadienyl)-6-methoxy-1H-1,3-benzimidazole Monooxalate

To a suspension of sodium hydride (0.25 g, 11 mmol) in dimethylformamide (10 mL) at 0° C. under nitrogen was added 6-methoxy-2-mercaptobenzimidazole (1.98 g, 11 mmol) in dimethylformamide (20 mL). The solution was allowed to stir to ambient temperature, then geranyl chloride (1.9 g, 11 mmol) was added and the reaction mixture stirred at 90° C. overnight. Evaporation of the solvent gave a residue which was dissolved in $CH_2Cl_2$, washed with $H_2O$ and dried over $Na_2SO_4$. Evaporation and flash chromatography (Merck Kieselgel, 5% $MeOH/CH_2Cl_2$) gave 1-(3,7-dimethyl-2,6(E)-octadienyl)-6-methoxy-1H-1,3-benzimidazole (free base) (2.4 g, 77%) as a 1:1 mixture of 5- and 6-methoxy isomers. Conversion to the oxalate salt in diethyl ether filtration 10 minutes after addition of oxalic acid gave 500 mg of the title compound as a white solid (pure 6-methoxy by 400 MHz NMR with NOE). m.p. 90°–94° C. NMR (DMSO-$d_6$)δ8.3(s,1H), 7.68(d,J=2 Hz,1H), 7.63(d,J=9 Hz,1H), 7.23(m,1H), 5.3 d,J=7 Hz, 1H), 5.0(m,1H), 4.90(d,J=8 Hz,2H), 2.0(m,4H), 1.70(s,3H), 1.58(s,3H), 1.55(s,3H).
Anal. Calcd. for
$C_{18}H_{24}N_2O.(COOH)_2$: C,64.15; H,7.00; N,7.48.
Found: C,63.73; H,6.96; N,7.45.

EXAMPLE 19

1-[3,7-Dimethyl-2,6(E)-octadienyl]-2-hydroxymethyl-1H-1,3-benzimidazole Hydrochloride.¼$H_2O$ A solution of 2-hydroxymethyl-2-mercaptobenzimidazole (2.68 g, 20 mmol), geranyl chloride (3.44 g, 20 mmol), tetrabutylammonium iodide (0.740 g, 2 mmol), saturated $NaHCO_3$ (50 mL) and $CH_2Cl_2$ (40 mL) was stirred at ambient temperature for 72 hours. The methylene chloride layer was separated, washed with water and dried over $Na_2SO_4$. Evaporation and flash chromatography (Merck Kieselgel, 5% $MeOH/CH_2Cl_2$) gave 1-[3,7-dimethyl-2,6(E)-octadienyl]-2-hydroxymethyl-1H-1,3-benzimidazole free base) (1.45 g) which was converted to its hydrochloride salt, a gray solid. m.p. 120°–123° C. NMR (DMSO-$d_6$)δ7.80(m,4H), 5.20(m,6H), 2.90(s,3H), 2.10(m,4H), 1.64(s,3H), 1.62(s,3H).
Anal. Calcd. for
$C_{18}H_{24}N_2O.HCl.\frac{1}{4}H_2O$: C,64.66; H,7.48; N,8.38.
Found: C,64.72; H,7.82; N,8.40.

EXAMPLE 20

5 (and 6)-Chloro-2-methyl-1-(3,7-dimethyl-2,6(E)-octadienyl)-1H-1,3-benzimidazole Monohydrochloride.¼$H_2O$ To a suspension of sodium hydride (0.69 g, 30 mmol) in dimethylformamide (20 mL) at 0° C. under nitrogen was added 5 (and 6)-chloro-2-methyl-2-mercaptobenzimadazole (4.0 g, 30 mmol) in dimethylformamide (30 mL). The solution was stirred to ambient temperature, then geranyl chloride (5.2 g, 30 mmol) was added, and the reaction mixture was stirred at 90° C. overnight. Evaporation of the solvent gave a residue which was dissolved in $CH_2Cl_2$, washed with water and dried over $Na_2SO_4$. Evaporation and flash chromatography (Merck Kieselgel, 5% $MeOH/CH_2Cl_2$) gave 5 (and 6)-chloro-2-methyl-1-(3,7-dimethyl-2,6(E)-octadienyl)-1H-1,3-benzimidazole (free base) which on conversion to its hydrochloride salt and recrystallization from isopropyl alcohol gave the title compound as a white solid mixture of the 5 and 6 chloro isomers. m.p. 98°–108° C. NMR (DMSO-$d_6$)δ7.75(m,3H), 5.30(t,J=7 Hz,1H), 5.10(d,J=7 Hz, 2H), 5.0(t,J=7 Hz,1H), 2.90(s,3H), 1.85(s,3H), 1.52(s,3H), 1.50(s,3H).
Anal. Calcd. for
$C_{18}H_{23}ClN_2.HCl.\frac{1}{4}H_2O$: C,62.88; H,7.19; N,8.14.
Found: C,62.97; H,7.17; N,8.13.

EXAMPLE 21

1-(3,7-Dimethyl-2,6(E)-octadienyl)-2-(4-methylthiophenyl)-1H-1,3-benzimidazole Monooxalate.$H_2O$ A neat mixture of 2-mercaptobenzimidazole (2.2 g, 20 mmol) and p-methylthiobenzoic acid (3.36 g, 20 mmol) was stirred at 120° C. for 96 hours under nitrogen, flash chromatographed (Merck Kieselgel, 10% $MeOH/CH_2Cl_2$), evaporated, dissolved in $CH_2Cl_2$, and dried over $Na_2SO_4$. Evaporation of the solvent gave 2-(4-methylthiophenyl)-2-mercaptobenzimidazole (0.3 g, 2.3 mmol) which was dissolved in $CH_2Cl_2$ (10 mL), 2N $NaOH/H_2O$ (8 mL), tetrabutylammonium iodide (0.075 g, 0.2 mmol) and geranyl chloride (0.4 g, 2.3 mmol), and stirred under nitrogen for 96 hours at ambient temperature. Evaporation and flash chromatography (Merck Kieselgel, 10% $MeOH/CH_2Cl_2$) gave 1-(3,7-dimethyl-2,6(E)-octadienyl)-2-(4-methylthiophenyl)-1H-1,3-benzimidazole (660 mg) as an oil which was converted to its oxalate salt to give a light brown solid (580 mg) m.p. 109°–112° C. NMR (DMSO-$d_6$) δ7.4(m, 8H), 5.27(m, 1H), 4.93(m, 1H), 4.88(br, 2H), 2.58(s, 3H), 2.0(br, 4H), 1.68(s, 3H), 1.58(s, 3H), 1.55(s, 3H).

Anal. Calcd. for
$C_{24}H_{28}N_2S.(COOH)_2.H_2O$: C,84.88; H,8.55; N,5.78.
Found: C,84.70; H,8.25; N,6.02.

EXAMPLE 22

Isolated Parietal Cell Assay

Using the procedures described in Batzri, S. et al., *Biochemica et Biophysica Acta* 508, 328 (1978), and Soll, H., *Am. J. Physiol.* 238, G366 (1980), the example compounds were tested for their ability to inhibit $^{14}C$-aminopyrine accumulation in stimulated parietal cells.

Parietal cells were isolated from the fundic mucosa of rabbit stomachs by a four-stage collagenese digestion process. The supernatant fraction from the last two stages of this process contain the individual parietal cells.

This cell suspension was centrifuged and reconstituted in a modified Hank's buffer to contain $1-2 \times 10^6$ cells/ml. The cells in this suspension were then evaluated for their ability to accumulate $^{14}C$-aminopyrine ($^{14}C$-AP), a weak base which has been shown to accumulate in acidic environments such as the parietal cell. The accumulation of $^{14}C$-AP is stimulated by histamine, and is blocked by $H_2$ antagonists.

The cells were incubated with $2 \times 10^6$ cpm $^{14}C$-AP, with various concentrations of histamine, $1 \times 10^{-5}M$ isobutylmethylanthine, and example compounds added in a 20 µl volume of buffer or dimethylsulfoxide. The flasks were incubated in a shaking water bath at 37° C. and gassed with 95% $O_2$, 5% $CO_2$ for 20 minutes. Three aliquots were then taken from each flask, and cell pellets were collected by centrifugation. The pellets were then solubilized with Protosol (NEN) and the radioactivity determined by liquid scintillation spectrometry.

The data for the example compounds is presented in Table 1 below as the $IC_{50}$, i.e. the concentration of compound required to inhibit $^{14}C$-AP accumulation in the stimulated parietal cell by 50%.

EXAMPLE 23

Isolated $H^+/K^+ATPase$ Assay

Using the procedures described in Eibl, H. et al., *Analytical Biochemistry* 30, 51 (1969), Ganser, A. L. et al., *Biochem. Biophys. Acta* 307, 169 (1973), and Beil, W. et al., *Br. J. Pharmac.* 82, 651 (1984), the example compounds were tested for their ability to inhibit the $H^+/K^+ATPase$ enzyme in the vesicular membranes from rabbit gastric mucosa. The $H^+/K^+ATPase$ enzyme activity is present in microsomes prepared from a crude homogenate of rabbit gastric mucosa using differential centrifugation.

Assays were conducted in duplicate tubes in a 1 mL reaction volume consisting of 50 mM Tris buffer, 2mM $MgCl_2$, ±10 mM KCl, 10 µl of example compound in dimethylsulfoxide and 20–30 µg of protein. The tubes were preincubated for 10 minutes in a 37° C. shaking water bath before the substrate, ($Na_2ATP$) was added. The mixture was then incubated for 15 minutes at 37° C. The reaction was stopped with 1 mL of 14% TCA and the tubes were centrifuged at 2000 rpm for 10 minutes.

The amount of inorganic phosphate (Pi) present in each sample was compared to a potassium phosphate standard curve. The data for the example compounds is presented in Table 1 below as the $IC_{50}$, i.e. the concentration of compound required to inhibit the K+ stimulated response by 50%.

TABLE 1

| Example Compound | Example 22 Antisecretory Activity in Parietal Cell | | Example 23 Isolated $H^+/K^+ATPase$ Assay $IC_{50}$ |
|---|---|---|---|
| | HI | DcAMP | |
| 1 | 1.3 | 2.15 | NA |
| 2 | 2.3 | 3.5 | 5.0 |
| 3 | 3.1 | 2.3 | 5.6 |
| 4 | 0.7 | 2.1 | NA |
| 5 | 4.0 | 19.0 | 3.2 |
| 6 | 0.46 | 0.51 | NA |
| 7 | 2.2 | 2.2 | NT |
| 8* | 40 | 33.3 | 72.0 |
| 9 | 2.0 | 1.25 | 3.0 |
| 10 | 1.7 | 1.1 | NA |
| 11 | 2.8 | 3.1 | NT |
| 12 | 1.9 | 1.0 | NA |
| 13 | 1.3 | NA | NT |
| 14 | 2.4 | NA | NT |
| 15 | 2.4 | 2.9 | 9.6 |
| 16 | NT | NT | NT |
| 17 | 1.7 | 1.1 | NA |
| 18 | 0.8 | 0.86 | 28.0 |
| 19 | 2.0 | 3.3 | 15.0 |
| 20** | 0.43 | 1.6 | 10.0 |
| 21 | 40 | 3.0 | 0.86 |

*compound is the sulfoxide derivative.
**Mixture of C-5 and C-6 isomers.

What is claimed is:

1. The compound selected from the group consisting of 2-[(3,7-dimethyl-2,6(E)-octadienyl)-thio]-1H-1,3-benzimidazole, 5-chloro-2-[(3,7-dimethyl-2,6(E) octadienyl)thio]-1H-1,3-benzimidazole, 6-chloro-5-fluoro-2-[(3,7-dimethyl-2,6(E)-octadienyl) thio]-1H-1,3-benzimidazole.¼hydrate, 2-[(3,7-dimethyl-2,6(E)-octadienyl)thio]-5-methoxy-1H-1,3-benzimidazolemonooxalate, 1-(3,5-dimethyl-4-methoxy-2-pyridylmethyl)-2-[(3,7-dimethyl-2,6 (E) -octadienyl) thio]-1H-1,3-benzimidazole monooxalate hemihydrate and 5-trifluoromethyl-2-[3,7-dimethyl-2,6(E)-octadienyl)thio]-1H-1,3-benzimidazole.

2. The compound selected from the group consisting of 3S(+)-2-(3,7-dimethyl-6-octen-1-yl)-thio]-1H-1,3-benzimidazole, (+)-2-[3,7-dimethyl-6-octen-1-yl)sulfinyl]-1H-1,3-benzimidazole monooxalate, 1-(3,5-dimethyl-4-methoxy-2-pyridylmethyl)-2-[(3,7-dimethyl-6-octen-1-yl)thio]-1H-1,3-benzimidazole monooxalate, 1- 3,7-dimethyl-2,6(Z)-octadienyl)-2-[(3,7-dimethyl-2,6(Z)-octadienyl)-thio]-1H-1,3-benzimidazole monooxalate, 2-[(3,7-dimethyl-2,6 Z) -octadienyl) thio]-1H-1,3-benzimidazole.¼hydrate, 2-octylthio-1H-1,3-benzimidazole, 5-methoxy-2-octylthio-1H-1,3-benzimidazole hemioxalate monohydrate and 5-chloro-2-octylthio-1H-1,3-benzimidazole.

3. A pharmaceutical composition comprising as an active ingredient an effective amount of the compound of claim 1, and a suitable pharmaceutical carrier.

4. A pharmaceutical composition comprising as an active ingredient an effective amount of the compound of claim 2, and a suitable pharmaceutical carrier.

5. A method of treating ulcers in mammals by administering an effective amount of the compound of claim 1.

6. A method of treating ulcers in mammals by administering an effective amount of the compound of claim 2.

* * * * *